United States Patent [19]

Bauman

[11] Patent Number: 4,815,451

[45] Date of Patent: Mar. 28, 1989

[54] SUBMERGIBLE LARYNOGOSCOPE WITH SEALED HOUSING FOR BATTERY

[76] Inventor: Jack Bauman, 3212 Nebraska, Santa Monica, Calif. 90404

[21] Appl. No.: 129,147

[22] Filed: Dec. 7, 1987

Related U.S. Application Data

[63] Continuation-in-part of Ser. No. 3,174, Jan. 27, 1987, Pat. No. 4,729,367, which is a continuation-in-part of Ser. No. 830,280, Feb. 11, 1986, Pat. No. 4,669,449.

[30] Foreign Application Priority Data

| Feb. 6, 1987 | [CA] | Canada | 529164 |
| Feb. 9, 1987 | [ID] | Indonesia | 11963 |
| Feb. 16, 1987 | [BR] | Brazil | 8700704 |
| Feb. 16, 1987 | [MY] | Malaysia | PI8700145 |
| Feb. 16, 1987 | [NG] | Nigeria | 35/87 |
| Feb. 17, 1987 | [AU] | Australia | 68884/87 |
| Feb. 18, 1987 | [EP] | European Pat. Off. | 87301383 |
| Feb. 18, 1987 | [IN] | India | 142/DE1/87 |
| May 30, 1987 | [JP] | Japan | 62-137573 |

[51] Int. Cl.[4] .............................................. A61B 1/06
[52] U.S. Cl. ...................................................... 128/11
[58] Field of Search ............... 128/6, 10, 11; 362/118, 362/152, 202; 179/111 E

[56] References Cited

U.S. PATENT DOCUMENTS

| 1,165,232 | 12/1915 | De Zeng | 128/11 |
| 2,433,705 | 12/1947 | Palmeter | 128/10 |
| 3,579,269 | 5/1971 | Ostersen | 128/11 |
| 4,273,112 | 6/1981 | Heine et al. | 128/11 |
| 4,531,178 | 7/1985 | Uke | |
| 4,574,784 | 3/1986 | Soloway | 128/11 |
| 4,592,343 | 6/1986 | Upster | 128/11 |
| 4,669,449 | 6/1987 | Bauman | 128/11 |
| 4,729,367 | 3/1988 | Bauman | 128/11 |

FOREIGN PATENT DOCUMENTS

| 0169497 | 1/1986 | European Pat. Off. |
| 1566116 | 1/1970 | Fed. Rep. of Germany |
| 2358042 | 6/1974 | Fed. Rep. of Germany |
| 1205975 | 9/1970 | United Kingdom |

Primary Examiner—Max Hindenburg
Attorney, Agent, or Firm—William W. Haefliger

[57] ABSTRACT

A fluid submersible laryngoscope includes a hollow handle to contain a power supply such as dry cell means. A terminal pin is carried by the handle, and structure is provided to place that pin in electrical energy transmitting relation with a light bulb, the blade insertible into a patient's mouth to illuminate the throat area. Sealing structure is provided between the terminal pin and handle to block access of external fluid into the hollow handle, whether or not the blade is attached to the handle, and when the handle is submerged in fluid.

29 Claims, 5 Drawing Sheets

SUBMERGIBLE LARYNOGOSCOPE WITH SEALED HOUSING FOR BATTERY

BACKGROUND OF THE INVENTION

This application is a continuation-in-part of Ser. No. 003,174, filed Jan. 27, 1987, U.S. Pat. No. 4,729,367, which is a continuation-in-part of Ser. No. 830,280, filed Feb. 11, 1987, U.S. Pat. No. 4,669,449.

This invention generally relates to examining devices such as laryngoscopes and particularly to an improved submersible device of this type.

Laryngoscopes generally comprise a blade and a cooperating handle which are connected together in an L-shaped configuration. The hollow handle normally serves as an enclosure for a power supply such as one or more dry cells which are adapted to energize a light bulb. The light from the bulb emanates from the distal end of the blade or is carried by fiber optic means, to illuminate the patient's mouth and larynx during the examination thereof by medical personnel. A surface on the blade is used to press against the tongue and mandible of a patient in a supine position in order to prevent the patient's tongue from obstructing the visual examination of the larynx by medical personnel.

While the instrument is useful for examining the larynx, the primary function of the laryngoscope is to expose the larynx in order to faciliate the insertion of an endotracheal tube. The surface of the laryngoscope blade adjacent the handle is urged against the tongue and mandible to expose the larynx in such procedures and the opposite blade surface is positioned opposing the upper front teeth of the patient.

The handle and blade are desirably re-usable, and must be cleaned thoroughly after use, since fluid from the patient's mouth can contaminate the equipment. However, washing of the handle, presents the problem of fluid gaining access to the power supply, i.e. dry cells, within the handle hollow, as via one or both ends of the handle. This is a particular problem when the light bulb is carried at the end of the handle to which the blade attaches, as cleaning fluid can leak past the bulb into the handle to cause bulb circuit malfunction.

Two solutions to this problem are included, in my U.S. Pat. Nos. 4,679,547 and 4,669,449.

SUMMARY OF THE INVENTION

It is a major object of the invention to provide a solution to the above problem, improving upon the apparatus of said patents, through provision of a fluid or liquid submersible laryngoscope including a hollow handle to contain power supply means, a blade to be inserted into a patient's mouth, and means to removably attach the blade to an end portion of the handle in a substantially L-shaped configuration, the improvement comprising (a) a light source carried by the laryngoscope, (b) means to place the light source in electrically energizing relation with the power supply means when the blade is attached to the handle, including a contact located at the end of the hollow handle to be contacted by the blade when the blade is attached to the handle, (c) a tubular body receiving the contact for endwise movement relative to the body, the body carried by the handle in peripherally sealed relation therewith, (d) and means sealing off between the contact and body.

As will appear, the means sealing off between the contact and body may include either or both of a displaceable sealant such as an elastomer within the body, or an O-ring about the contact, for preventing external fluid access into the hollow handle whether or not the blade is attached to the handle, and whether or not the handle is submerged in fluid. That elastomer may consist of silicone rubber.

Further, a conductive spring, such as a compression coil spring, is typically received in the body bore to resiliently urge the contact toward the blade for restoring the contact to a position for blade plunger engagement. The sealant may embed the spring, but does not prevent spring functioning, as described.

In addition, the invention is especially adaptable for use in a laryngoscope that accepts different construction blades, i.e. blades that have plungers at different locations to engage contacts for light bulb energization. Thus, the device may include:

(e) second means to place the light source in electrically energizing relation with the power supply means when an alternate blade is attached to the handle, including a second contact extending at the end of the hollow handle to be contacted by the blade when said alternate blade is attached to the handle, (f) a second tubular body receiving the second contact for endwise movement relative to the second body, the second body carried by the handle in peripherally sealed relation therewith and in offset but generally parallel relation to the first mentioned body, (g) and means sealing off between the second contact and second body whether or not there is endwise movement of the second contact.

The second means sealing off between the second contact and second body may likewise include either or both of a sealant and an O-ring, as described above; and a second spring may be located in the second tubular body to resiliently urge the second contact toward the blade, for engagement by a blade carried plunger. One or both of the two contacts, as described, may be received inwardly of the end of the tubular body.

The handle may, in this regard, include a tubular head (which may be metallic) carrying the tubular body, or two tubular bodies. The handle may also include a shank removably attached to the head, allowing quick removal of the head for replacement of batteries in the shank. Sealing means between the head and shank is provided by an elastomeric washer or O-ring.

A compression spring is provided between an end cap on the handle and battery means in the handle, for urging the battery means toward and into electrical contact with a metallic plug carried by the tubular body, that plug being in electrical communication with the contact or via the spring in the hollow body.

Also, an end cap may be removably attached to the end of the handle, remote from the blade, and second sealing means may be provided between the cap and handle to block access of external fluid into the hollow handle. In this regard, the handle and end cap are typically metallic, and the second sealing means comprises an elastomeric O-ring or washer. The blade itself is metallic and may carry the light bulb.

These and other features and advantages of the invention will become more apparent from the following detailed description when taken in conjunction with the accompanying drawings:

BRIEF DESCRIPTION OF THE DRAWINGS

In these drawings, all corresponding parts are numbered the same.

DETAILED DESCRIPTION OF THE INVENTION

Figure 1:
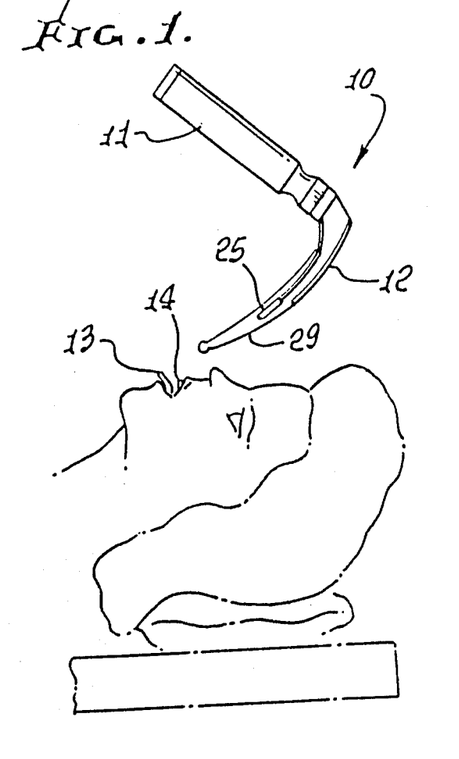
FIG. 1 is a side elevational view of a laryngoscope preparatory to being used on a patient which embodies features of the invention.

Reference is made to the drawings which illustrate a laryngoscope embodying features of the present invention. The instrument is intended for use by medical personnel in the examination of a patient's mouth and larynx and particularly to expose the larynx to facilitate the insertion of an endotracheal tube. As shown in FIG. 1, the laryngoscope 10, which comprises a handle 11 and blade 12, is utilized to depress the patient's tongue and mandible 13.

One form of means used to couple the blade 11 to the handle 12 is illustrated in FIGS. 2-6. As shown therein, the upper end of the handle 11 has an open channel 15, which is provided with a pivot rod 16 extending between flanges 17. The inner side of one flange has a groove or dimple 19 adapted to seat a spring urged detent 20 projecting at one side surface 18 of boot-shaped appendage 22 or the blade.

The boot shaped appendage 22 interfits into the open channel 15 and is mounted therein in a pivotal fashion. The front end 23 of the boot shaped appendage 22 is hooked under the pivot rod 16 during the pivotal mounting thereof, in a conventional fashion. To mount the blade onto the handle 11, the appendage 22 of the blade 12 is inserted into the open top channel 15 with a pivotal motion so that the front end 23 rotates under the pivot rod 16. i.e. from FIG. 3 to FIG. 4 condition. The detent 20 moves into engagement with the groove 19 provided in the surface 18, to thereby snap retainer appendage 22 into firm interfit with the pivot rod 16, as the blade moves from ready position, as shown in FIG. 3, to fixed position seen in FIG. 4.

Preferably, a light switch or contact 24 is provided at the bottom of the channel 15 in a position so that is is activated only when the blade 12 is rotated and locked into an operating position. A light source 25 such as an incandescent bulb is provided on the blade and is energized when the light switch 24 is activated. As shown in FIG. 3, when the blade 12 is initially mounted on the handle 11, the blade 12 is in a ready position on the handle 11 but a contact 26a on the bottom surface 26 of the appendage 22 does not activate, i.e. engage the light contact. Further rotation of the blade 12 causes the detent 20 to engage the groove 19, and to thereby lock the blade 12 in an operating position and simultaneously therewith to cause contact 26a to engage, i.e. activate the light contact 24, which in turn energizes the light source 25.

Figure 2:
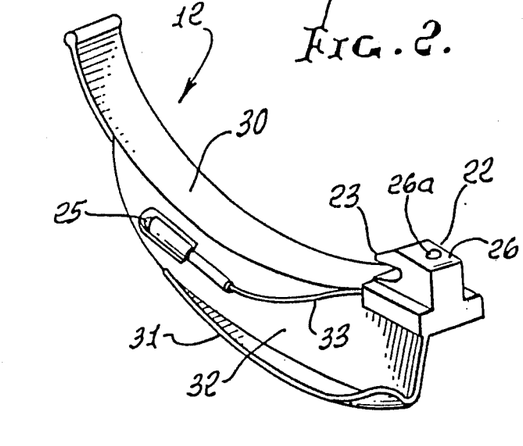
FIG. 2 is a perspective enlarged view of the blade of the laryngoscope shown in FIG. 1.
Figure 2A:
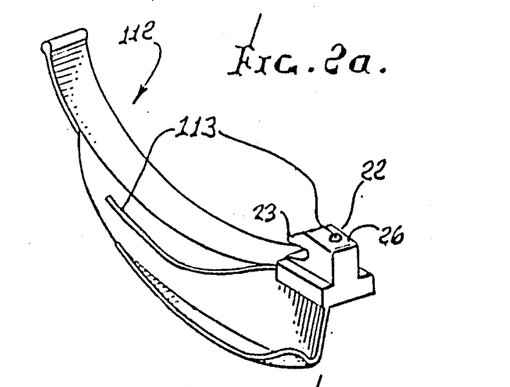
FIG. 2a is a perspective enlarged view of a fiber optics blade.
Figure 3:
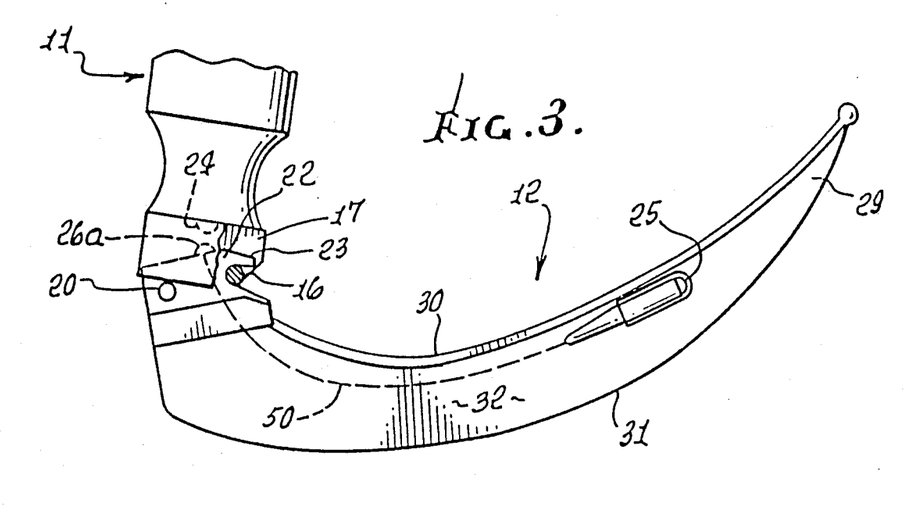
FIG. 3 is a side elevational view partially in section of the laryngoscope with the blade in a ready position.
Figures 4, 5, 6, 7:
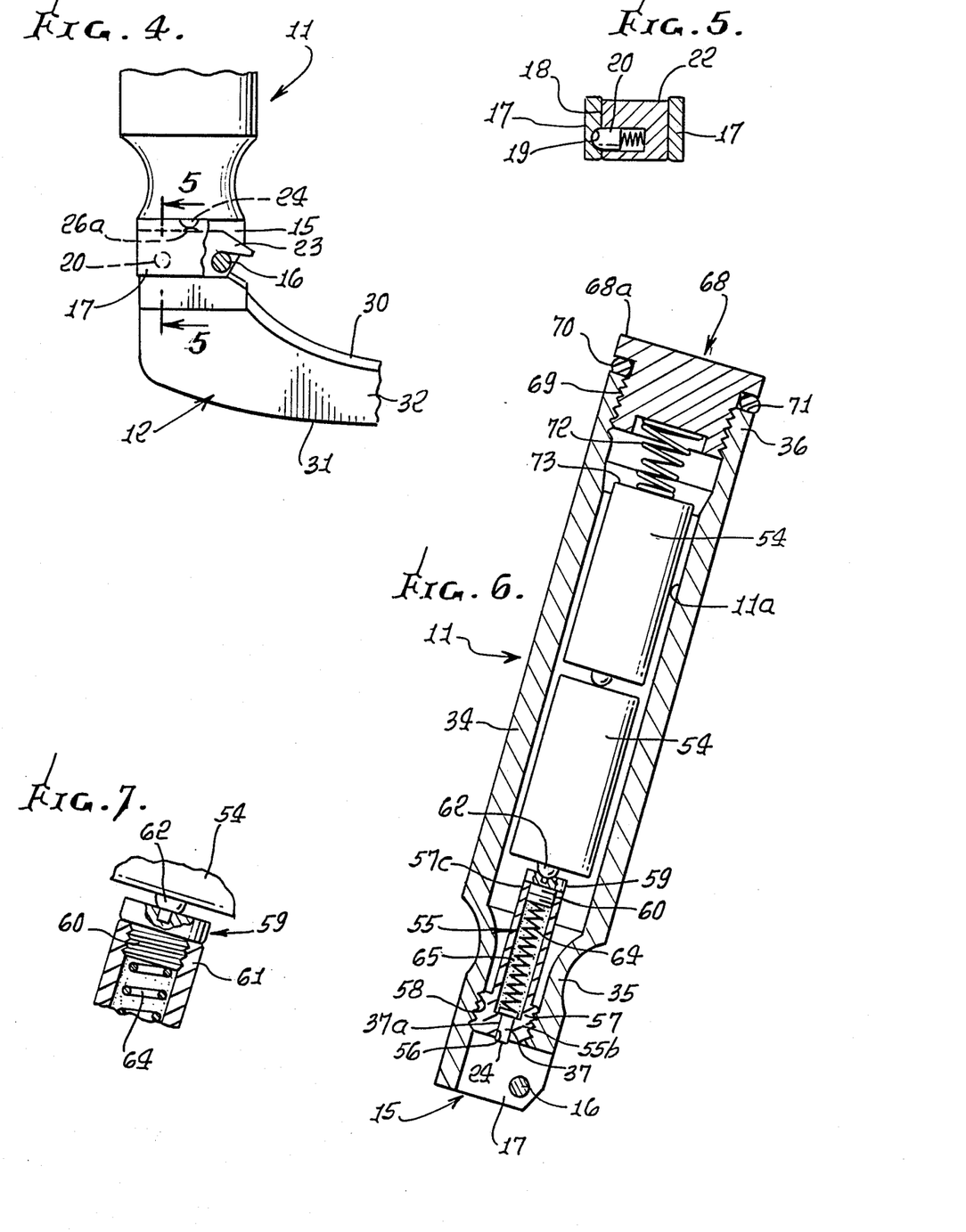
FIG. 4 is a partial side elevational view, partially in section, of the laryngoscope with the blade in the operative position.
FIG. 5 is a cross sectional view taken along the lines of 5—5 shown in FIG. 4.
FIG. 6 is a cross sectional view of the handle.
FIG. 7 is an enlarged view of dry cell engagement with an end closure.

As best shown in FIGS. 2-4, light is directed from the light source 25 to ensure the proper illumination of a patient's mouth and larynx when the laryngoscope is being used. The light is located near the end 29 of the blade 12 so that, when the blade 12 is rotated into its final operating position, the contact 26a is immediately adjacent to and engages the terminal 24 so that there is a reliable and efficient electrical coupling from the positive pole of the bulb to the positive pole of the dry cell. The "ground" of the bulb is in contact with the metal blade, and therefore in electrical continuity with the ground of the dry cell. Alternatively, the light source may be at the end of the handle, and a light pipe used to conduct light along and to the end of the blade. See FIG. 2a showing blade 112, and fiber optics light pipe 113.

The illustrated blade has a lower portion 30, an upper section 31, and a wall or web 32.

The handle 11, which is typically metallic, has an internal cavity 11a which is adapted to hold one or more battery units 54 (see FIG. 6) which supply electrical energy to light source 25.

The handle comprises a tubular body 34 having a reduced diameter end 35, and opposite end 36. The contact 24 is advantageously formed at the head of an electrically conductive terminal pin 37 located at handle end 35. The pin is placed in electrical energy transmitting relation with the light source, by means such as that referred to above.

Also provided is first fluid sealing means, located between the terminal pin and handle to block access of external fluid into the hollow handle, whether or not the blade is attached to the handle, and whether or not the handle is submerged in fluid. As shown, the first fluid sealing means comprises a tubular insulative (and typically rigid) body 55 carrying the terminal pin, the conductive pin having a shank 37a in fluid sealing and sliding relation with a bore 56 defined by the insulative body 55, the latter having an exterior generally annular surface 57 in fluid sealing enegagement with a bore 58 defined by the handle. Surfaces 57 and 58 may advantageously be threaded, and be in tight compressive engagement to define a good fluid seal.

Also shown is an electrically conductive end closure or plug 59 attached as by threading 60 to an end 57c of said body 55 remote from the terminal 24, said closure providing a current passing connection between the power source and said pin 37. Note that dry cell terminal 62 engages conductive metallic closure 59, which is carried on the insulative body 55.

Figure 13:
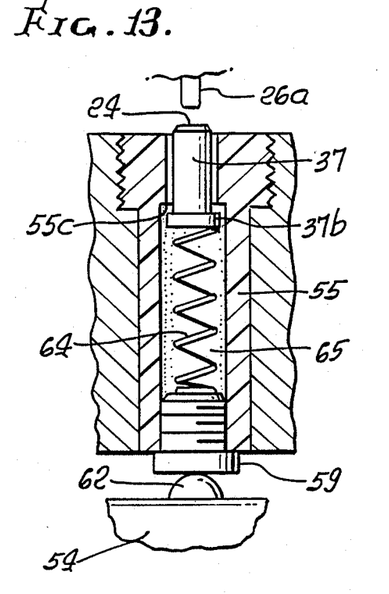
FIG. 13 is an enlarged section showing a terminal pin, tubular body and spring.

A metallic and conductive compression spring 64, in the form of a coil, extends between the end closure 59 and the pin 37, and is soldered to these elements, to provide an electrical current path therebetween, and within said protective and insulative tubular body 55. The spring resiliently urges the contact toward the blade, and toward the position shown, and a head 37b on the pin engages an internal shoulder 55c on the body to limit pin excursion toward the blade. See FIG. 13.

Sealant 65 fills or substantially fills the interior of the tubular body 55, embedding the spring, to block external fluid access into the hollow handle. That sealant is elastomeric and may consist of silicone rubber. When contact 26a engages contact or terminal 24, to displace the pin 37 inwardly against force exerted by the spring, an electrical path is established between 26a, 24, 37, 64, 59 and 62. The ends of the spring are typically soldered to the head 37a and to brass (conductive metal) closure cap 59.

An end cap 68 is removably attached to the end 36 of the handle, remote from the blade, and second fluid sealing means is provided between the cap and handle to block access of external fluid into the hollow handle, via end 36. In this regard, the cap may have threaded attachment at 69 to the handle, the cap and handle and typically consisting of conductive metal. Said second fluid sealing means may comprise an elastomeric O-ring 70 compressed between cap flange 68a and handle end 71. Element 70 may be a rubber washer.

An electrically conductive coil spring 72 is located between the cap 68 and the end 73 of one battery 54, to establish a ground.

After use, the blade is decoupled from the handle by simply rotating the blade 12 toward the handle 11 (interrupting the electrical circuit) and then pushing upwardly on the blade 12 to disengage or unhook the front end 12 of appendage 22 from the pivot rod 16. The blade and handle being water tight, can be washed, sterilized and reused.

Although a specific embodiment of the invention is described herein in connection with laryngoscopes, it is clear the invention can be employed in other examining devices.

Figure 14:
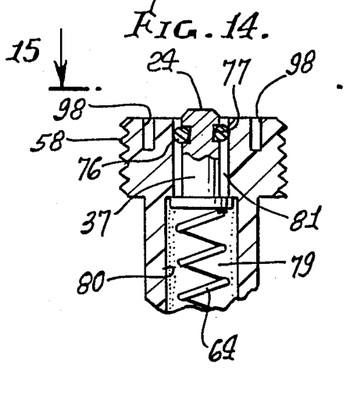
FIG. 14 is a fragmentary view like FIG. 13, but showing a modification.

Referring now to FIG. 14, an O-ring 76 is seated in annular groove 77 in the pin 37, so that the periphery of the O-ring slidably engages the bore 78 of the body 55, inwardly of threading 58, on the head of the body. Thus, additional sealing effect is produced; yet conducting spring 64 is sufficiently strong (i.e. sufficiently compressed) to restore the pin upwardly, after the contact 26a in the blade has displaced the pin 37 inwardly. Space 79 defined by the body bore 80 may also be filled with elastomeric or viscous sealant as referred to above, and that sealant may extend about the pin, in annular gap 81. A rotating tool may engage holes 98, for disassembly.

Referring now to FIGS. 8–12, the handle of the laryngoscope includes a head 84 carrying the tubular insulative body 55, axially of the head, and a tubular shank 85 extending coaxially with the head. The shank 85 carries the power supply battery or batteries, and the head is attached to the other end of the shank as by cooperative threading at 86. A fluid sealing means such as an elastomeric O-ring or rubber washer 87 seals off between the head and shank.

Figure 8:
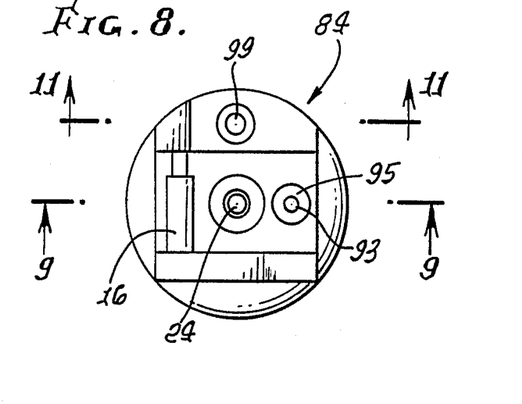
FIG. 8 is a top plan view of a modified handle that incorporates a head with two terminal pins and a light bulb.
Figure 11:
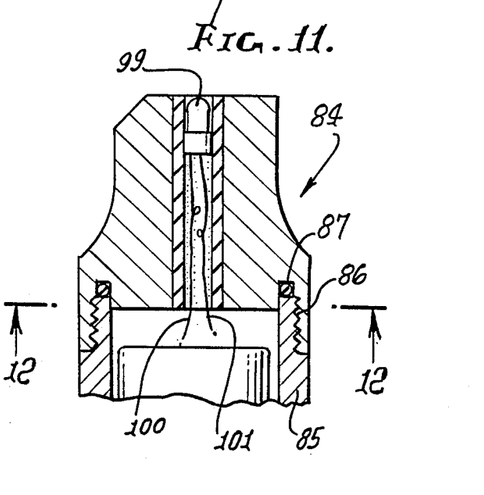
FIG. 11 is a section taken on lines 11—11 of FIG. 8.
Figure 12:
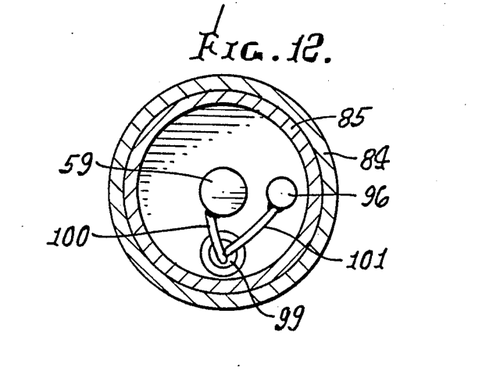
FIG. 12 is a section in plan on lines 12—12 of FIG. 11.

The head centrally carries the elements 55, 59, 64 and 37, as described above. In addition, it may also carry second means to place a light source in electrically energizing relation with the power supply means when the light bulb is in the handle (as in a fiber optic handle of the Upsher type, carrying a light bulb). Thus, either a blade containing a light bulb or a blade with a fiber optic bundle (see FIG. 2a) can be used on the same handle. See for example the central contact 26a on a blade 12 facing contact 24, in FIG. 9, as described above; and also see the offset contact 26a' on another and alternate blade 92 (of Upsher type) in FIG. 9a, and facing the second contact 93 sidewardly offset from contact 24, and also extending at the end of the handle. In this blade 92, a recess 92a replaces contact 26a, (but is at the location of 26a), so that the end contact 24 can enter the recess and seat be depressed. That second or alternate blade may be employed when it is desired to energize a light source such as a bulb 99 carried by the head, as best seen in FIGS. 8 and 11. Elastomer body 99a seals off against the head and the bulb to prevent fluid entrance. The bulb may also be sealed by a transparent window 140 across the end 99a' of the body.

Figure 9:
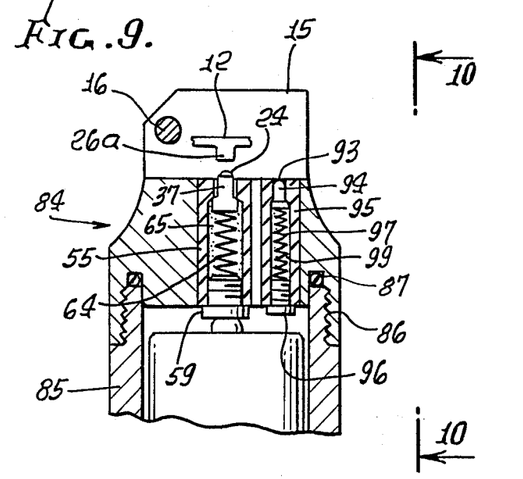
FIG. 9 is an elevation in section on lines 9—9 of FIG. 8.

In FIGS. 9, the elements of the second means to energize a light bulb in the handle correspond to the elements of the first means, to alternatively energize a light bulb in the blade as follows:

|  | elements of first means | elements of second means |
| --- | --- | --- |
| contact | 24 | 93 |
| pin | 37 | 94 |
| tubular body | 55 | 95 |
| end plug | 59 | 96 |
| spring | 64 | 97 |
| sealant | 65 | 199 |

Figure 9A:
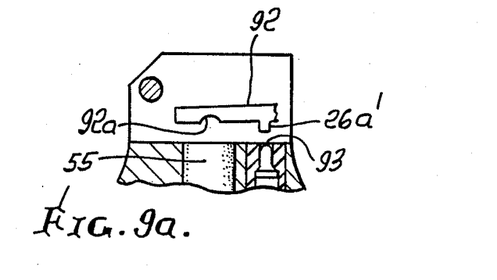
FIG. 9a is a view like FIG. 9 showing actuation of a different pin.
Figure 10:
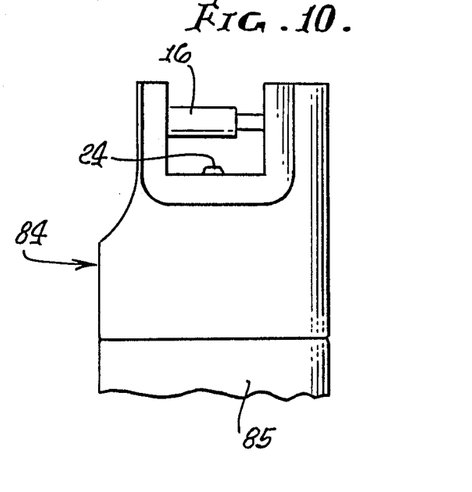
FIG. 10 is an external elevation taken on lines 10—10 of FIG. 9.

Note that contact or terminal 93 is recessed inwardly, slightly within the bore defined by insulative body 95, so that it cannot be engaged by the first blade 12 that carries the contact or plunger 26a; i.e., the plunger or contact 26a' on the second blade must enter the bore of body 95 to touch and depress contact 93 and 94. The use of springs 64 and 97 under compression assures good electrical engagement of the contacts 24 and 93 with the respective contacts or plungers 26a and 26a' on the two different blades.

The light source or bulb 99 comprises a glass envelope containing a filament connected to wires 100 and 101. One of such wires, such as 100, is connected as by soldering to the end plug 96, and the other wire 101 is connected to the plug 59 contacted by the battery contact 62. Thus, an electrical path is established from the battery terminal 62 to 59, 101, 99, 100, 96, 97, 93 and 26a' to the conductive metal case via the conductive metal blade, i.e. the battery return, or ground.

Figure 15:
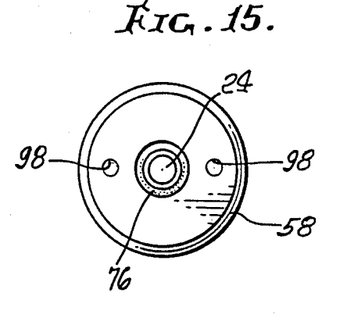
FIG. 15 is a view on lines 15—15 of FIG. 14.

As before, sealing (elastomeric) O-rings can be employed on and about the pins 37 and 94. Holes 98 in the upper end of body 55 allow entrance of a tool to rotate that body relative to head 84, as during installation. See FIGS. 14 and 15.

Figure 16:
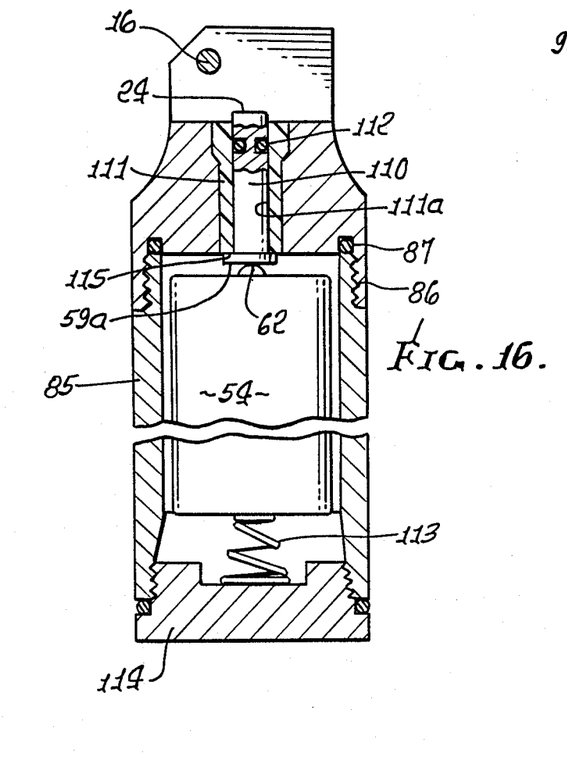
FIG. 16 is a section in elevation showing a further modification.

As an alternative method of sealing, as in FIG. 16, the conducting plug 59a engaged by the battery contact 62 is in direct electrical contact with the end contact 24, as via a one-piece electrically conductive rod 110 defining or carrying 59a and 24. That rod may consist of brass, and the means sealing off between the rod and bore 111a, of tubular body 111 is shown to include an elastomeric O-ring 112 fitted in an annular groove on the rod, near contact 24. Silicone sealant may be employed in the clearance between 110 and 111a, rod 110 being water tight but slidable relative to bore 111a.

A compression spring 113 (corresponding to spring 72 in FIG. 6) is located between end cap 114 and the battery or batteries, to urge battery contact 62 into engagement with a flange 59a on rod 110 and engageable with the end 115 of the body 111, to limit displacement of the rod and contact 24 toward the blade, i.e. to position 24 relative to the end 116 of the body prior to blade contact engagement with contact 24. This "ground" spring 113 permits downward displacement of the batteries and rod 110, in compression therewith.

Figure 17:
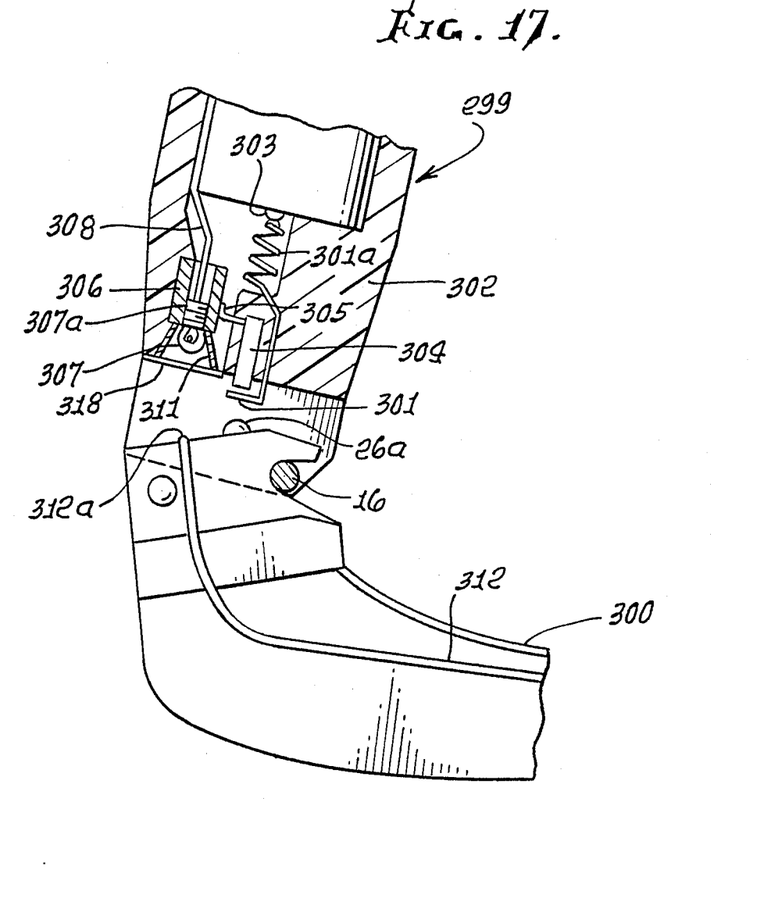
FIG. 17 is a side view of an alternate contact means at the end of a handle.

. Referring now to FIG. 17, a laryngoscope blade 300 pivots about a post 16 on the handle 299 as in FIG. 3, to bring a contact 26a on the blade toward and into engagement with a contact 301 on the handle, and exposed at the end of the handle. That contact extends back into the head in fixed sealed relation in insulative material body 302, to form a coil spring at 301a that is compressively engaged against the battery terminal 303. When blade terminal 26a engages contact 301, it deflects it backwardly to engage fixed terminal 304 completing an electrical circuit. The terminal 304 is also embedded in insulative plastic body 302, and has an arm 305 that projects into engagement with a conductive tube 306 mounted in the body. Tube 306 is internally threaded to receive the threaded stem 307a of light bulb 307. The end terminal of the bulb is electrically connected via wire 308 to the opposite end of the battery or batteries, or to the battery case, i.e. electrical ground.

When the bulb is energized by completion of the circuit, light is emitted, and reflected by reflector 311, to enter the end 312a of fiber optic light pipe 312. The latter extends along the blade 300, and light is transmitted from the end of the light pipe to illuminate the larynx. A transparent window is shown at 318. Modifications can be made without departing from the inventive concepts, as described.

I claim:

1. In a fluid submersible laryngoscope including a hollow handle containing power supply means, a blade to be inserted into a patient's mouth, and means to removably attach the blade to an end portion of the handle in a substantially L-shaped configuration, the improvement comprising:
   (a) a light source carried by the laryngoscope,
   (b) means to place the light source in electrically energizing relation with the power supply means when the blade is attached to the handle, including a contact located at the end of the hollow handle to be contacted by the blade when the blade is attached to the handle,
   (c) a tubular body receiving the contact for endwise movement relative to the body, the body carried by the handle in peripherally sealed relation therewith,
   (d) and means for sealing between the contact and body, said means including material extending at an end portion of the handle and acting as a sealant about said contact to be compressed when the blade is attached to the handle and displaced relatively toward said end portion of the handle, for preventing external fluid access into the hollow handle whether or not the blade is attached to the handle, and whether or not the handle is submerged in fluid.

2. The improvement of claim 1 wherein said means for sealing off between the contact and body includes a sealing O-ring within the body and about the contact for preventing external fluid access into the hollow handle whether or not the blade is attached to the handle, and whether or not the handle is submerged in fluid.

3. The improvement of claim 1 wherein said material acting as a sealant consists of a viscous material.

4. The improvement of claim 3 including an electrically conductive spring received in viscous material and urging said contact toward the blade.

5. The improvement of claim 4 wherein the conductive spring is a coil spring, and including an electrically conductive metallic plug carried by the body and contacting the end of the spring remote from the contact, and located for engaging a battery contact within the hollow handle.

6. The improvement of claim 4 wherein said spring is a compression spring urging the contact relatively away from the power supply means, and adapted to be compressed when the contact is displaced by the blade.

7. The improvement of claim 1 wherein said tubular body defines a flange having screw thread attachment to a bore defined by the handle, proximate said end thereof.

8. The improvement of claim 1 for use with different blades, including:
   (e) second means to place the light source to electrically energizing relation with the power supply means when an alternate and fiber optic type blade is attached to the handle, including a second contact extending at the end of the hollow handle to be contacted by the blade when said alternate blade is attached to the handle,
   (f) a second tubular body receiving the second contact for endwise movement relative to the second body, the second body carried by the handle in peripherally sealed relation therewith and in offset but generally parallel relation to the first mentioned body,
   (g) and means for sealing off between the second contact and second body whether or not there is endwise movement of the second contact.

9. The improvement of claim 8 wherein said second means sealing off between the second contact and second body includes displaceable sealant within the second body and about the second contact for preventing external fluid access into the hollow handle whether or not the blade is attached to the handle, and whether or not the handle is submerged in fluid.

10. The improvement of claim 9 wherein said sealant consists of a viscous material.

11. The improvement of claim 10 wherein said sealant consists essentially of one of the following:
   (i) silicone rubber
   (ii) grease
   (iii) elastomer.

12. The improvement of claim 8 wherein said second means for sealing off between the second contact and second body includes a sealing O-ring within the second body and about the second body for preventing external fluid access into the hollow handle whether or not the blade is attached to the handle, and whether or not the handle is submerged in fluid.

13. The improvement of claim 8 including a conductive metal spring received in the second body and urging the second contact toward the blade.

14. The improvement of claim 8 wherein said second contact is recessed inwardly from the end of the second tubular body.

15. The improvement of claim 8 including a second tubular body receiving the second contact, and wherein the handle includes a tubular metallic head carrying said tubular bodies which are non-metallic, and a shank carrying said power supply, the head attached to the shank, and fluid sealing means sealing off between the shank and head.

16. The improvement of claim 15 including a conductive compression spring carried by the head and biasing the second contact.

17. The improvement of claim 8 wherein the light source is carried by a head defined by the handle and includes a light bulb and means sealing off between the bulb and head.

18. The improvement of claim 1 including an end cap removably attached to the end of the handle remote from the blade, and other fluid sealing means between the cap and handle to block access of external fluid into the hollow handle.

19. The improvement of claim 18 wherein the handle and cap are electrically conductive and said second fluid sealing means comprises an elastomeric O-ring.

20. The improvement of claim 1 wherein said handle includes a head carrying said tubular body, and a shank carrying said power supply, the head attached to the shank, and fluid sealing means sealing off between the shank and head.

21. The improvement of claim 18 including a compression spring between the end cap and the power supply means and urging the power supply means into electrical contact with a metallic plug carried by said tubular body, the plug being in electrical communication with the contact.

22. In a fluid submersible laryngoscope including a hollow handle containing power supply means, a blade to be inserted into a patient s mouth, and means to removably attach the blade to an end portion of the handle in a substantially L-shaped configuration, the improvement comprising:
(a) a light source carried by the laryngoscope
(b) means to place the light source in electrically energizing relation with the power supply means when the blade is attached to the handle, including a contact located at the end of the hollow handle to be contact by the blade when the blade is attached to the handle,
(c) a tubular body receiving the contact for endwise movement relative to the body, the body carried by the handle in peripherally sealed relation therewith,
(d) and means for sealing between the contact and body, said means including material extending at an end portion of the handle and acting as a sealant about said contact to be compressed when the blade is attached to the handle and displaced relatively toward said end portion of the handle, for preventing external fluid access into the hollow handle whether or not the blade is attached to the handle, and whether or not the handle is submerged in fluid,
(e) said tubular body defining a flange having screw thread attachment to a bore defined by the handle, proximate said end thereof.

23. The improvement of claim 22 wherein said means for sealing off between the contact and body includes displaceable sealant within said body and about said contact for preventing external fluid access into the hollow handle, and whether or not the handle is submerged in fluid, and said sealant also embeds the spring or portion thereof.

24. The improvement of claim 22 wherein said means for sealing off between the contact and body includes a sealing O-ring within the body and about the contact for preventing external fluid access into the hollow handle whether or not the blade is attached to the handle, and whether or not the handle is submerged in fluid, and including a displaceable sealant within said body and embedding said spring.

25. In a fluid submersible laryngoscope including a hollow handle to contain power supply means, a blade to be inserted into a patient's mouth, and means to removably attach the blade to an end portion of the handle in a substantially L-shaped configuration, the improvement comprising:
(a) a light source carried by the laryngoscope,
(b) means to place the light source in electrically energizing relation with the power supply means including contact means located at the end of the hollow handle to be contacted when the blade is attached to the handle,
(c) a tubular body carrying the contact means,
(d) and means for sealing off between the contact means and body, and including displaceable material within said body and acting as a sealant about said contact means for preventing external fluid access into the hollow handle whether or not the blade is attached to the handle, and whether or not the handle is submerged in fluid.

26. The improvement of claim 25 wherein said contact means includes first and second electrical contacts which are interengaged in response to attachment of the blade to the handle.

27. The improvement of claim 25, including yieldable means biasing said first contact in a direction toward the blade, the first contact located at the exterior of the handle.

28. In a fluid submersible laryngoscope including a hollow handle, containing power supply means, a blade to be inserted into a patient's mouth, and means to removably attach the blade to an end portion of the handle in a substantially L-shaped configuration, the improvement comprising:
(a) a light source carried by the laryngoscope,
(b) means to place the light source in electrically energizing relation with the power supply means when the blade is attached to the handle, including a contact located at the end of the hollow handle to be contacted by the blade when the blade is attached to the handle,
(c) a tubular body receiving the contact for endwise movement relative to the body, the body carried by the handle in peripherally sealed relation therewith,
(d) and means for sealing off between the contact and body, including displaceable sealant within said body and and about said contact for preventing external fluid access into the hollow handle whether or not the blade is attached to the handle, and whether or not the handle is submerged in fluid, (e) said means to place the light source in energizing relation with the power supply means including elongated means embedded in the sealant and engaging the contact, within said tubular body.

29. The improvement of claim 28 wherein said elongated means extends lengthwise toward said power supply means, and including an electrically conductive metallic plug carried by the body and contacting the end of said elongated means remote from the contact, and located for engaging a battery contact within the hollow handle.

* * * * *